US007446182B1

(12) United States Patent
Georgiou et al.

(10) Patent No.: US 7,446,182 B1
(45) Date of Patent: Nov. 4, 2008

(54) RECOMBINANT ANTIBODIES FOR THE DETECTION AND NEUTRALIZATION OF ANTHRAX TOXIN

(75) Inventors: George Georgiou, Austin, TX (US); Brent L. Iverson, Austin, TX (US); Jennifer A. Maynard, Palo Alto, CA (US)

(73) Assignee: Board of Regents, The University of Texas System, Austin, TX (US)

( * ) Notice: Subject to any disclaimer, the term of this patent is extended or adjusted under 35 U.S.C. 154(b) by 584 days.

(21) Appl. No.: 10/288,269

(22) Filed: Nov. 5, 2002

Related U.S. Application Data

(60) Provisional application No. 60/332,849, filed on Nov. 5, 2001.

(51) Int. Cl.
*C12P 21/08* (2006.01)
(52) U.S. Cl. ............... 530/388.4; 530/387.9; 530/387.3; 530/864; 530/865; 530/866; 530/867; 530/809
(58) Field of Classification Search ............... 530/388.4, 530/387.9, 387.3, 389.5, 864–867, 809; 424/135.1, 424/800, 801, 139.1, 150.1, 802, 808, 809; 435/326
See application file for complete search history.

(56) References Cited

U.S. PATENT DOCUMENTS

| 5,601,823 | A | 2/1997 | Williams et al. | 424/167.1 |
|---|---|---|---|---|
| 6,329,156 | B1 | 12/2001 | Cirino et al. | 435/721 |
| 6,916,474 | B2 * | 7/2005 | Harvey et al. | 424/130.1 |
| 2005/0106647 | A1 | 5/2005 | Harvey et al. | 435/7.32 |
| 2005/0267294 | A1 | 12/2005 | Harvey et al. | 530/388.4 |

FOREIGN PATENT DOCUMENTS

| WO | WO 99/36569 A1 | 7/1999 |
|---|---|---|
| WO | WO 2005/023177 | 3/2005 |

OTHER PUBLICATIONS

Maynard et al. In: Abstracts of Papers of 216th National Meeting of the ACS, Boston, Massachusetts, #212, BIOT, Aug. 23-27, 1998.*
Rosovitz et al. J. Biol. Chem. 278: 30936-30944, May 2003.*
Harvey et al. PNAS 101: 9193-9198, Jun. 22, 2004.*
Maynard et al. Nature Biotechnol. 20: 597-601, Jun. 2002.*
Bradley et al., "Identification of the cellular receptor for anthrax toxin," *Nature*, 414:225-229, 2001.
Bull and Parrish, "A binding contract for anthrax," *Science*, 297:201-202, 2002.
Chen et al., "Isolation of high-affinity ligand-binding proteins by periplasmic expression with cytometric sceening," *Nature Biotechnology*, 19:537-542, 2001.
Daugherty et al., "Quantitative analysis of the effect of the mutation frequency on the affinity maturation of antibodies," *Proc. Natl. Acad. Sci., USA*, 97:2029-2034, 2000.
Ezzell et al., "Immunoelectrophoretic analysis, toxicity, and kinetics of in vitro production of the protective anitgen and lethal factor components of *Bacillus anthracis* toxin," *Infect. Immun.*, 45:761-777, 1984.
Ivins et al., "Influence of body weight on response of Fischer 344 rats to anthrax lethal toxin," *Applied and Environmental Microbiology*, 55:2098-2100, 1989.
Keller and Stiehm, "Passive immunity in prevention and treatment of infectious diseases," *Clin. Microbiol. Reviews*, 13:602-614, 2000.
Krebber et al., "Reliable cloning of functional antibody variable domains from hybridomas and spleen cell repertoires employing a reengineered phage display system," *J. Immunol. Methods*, 201:35-55, 1997.
Leppla, "Anthrax toxin," Chapter 19 In: *Handbook of Experimental Pharmacology*, 145:445-472, 2000.
Little et al., "Characterization of lethal factor binding and cell receptor binding domains of potective antigen of *Bacillus anthracis* using monoclonal antibodies," *Microbiology*, 142:707-715, 1996.
Little et al., "Passive protection by polyclonal antibodies against *Bacillus anthracis* infection in guinea pigs," *Infection and Immunity*, 65:5171-5175, 1997.
Little et al., "Production and characterization of monoclonal antibodies to the protective antigen component of *Bacillus anthracis* toxin," *Infect. Immun.*, 56:1807-1813, 1988.
Maynard et al., "Production against anthrax toxin by recombinant antibody fragments correlates with antigen affinity," *Nature Biotechnology*, 20:597-601, 2002.
Mourez et al., "Designing a polyvalent inhibitor of anthrax toxin," *Nature Biotechnology*, 19:958-961, 2001.
Pitt et al., "In vitro correlate of immunity in a rabbit model of inhalational anthrax," *Vaccine*, 19:4768-4773, 2001.
Sellman et al., "Dominant-negative mutants of a toxin subunit: an approach to therapy of anthrax," *Science*, 292:695-697, 2001.
Singh et al. "A dominant negative mutant of *Bacillus anthracis* protective antigen inhibits anthrax toxin in vivo," *J. of Biol. Chem.*, 276:22090-22094, 2001.
Turnbill et al., "Antibodies to Anthrax Toxin in Humans and Guinea Pigs and Their Relevance to Protective Immunity," Abstract, *Med. Microbiol. Immunol.*, 177:293-303, 1988.
Chen and Okayama, "High-efficiency tranformation of mammalian cells by plasmid DNA," *Mol. Cell Biol.*, 7(8):2745-2752, 1987.
Chen et al., "In vitro scanning saturation mutagenesis of all the specificity determining residues in an antibody binding site," *Protein Eng.*, 12:349-352, 1999.
Cirino et al., "Disruption of anthrax toxin binding with the use of human antibodies and competitive inhibitors," *Infection and Immunity*, 67:2957-2963, 1999.
Creighton, *Protein Structure: A Practical Approach*, p. 184-186, 1994.
Creighton, *Proteins: Structures and Molecular Properties*, p. 314-315, 1984.
Georgiou et al., "Display of heterologous proteins on the surface of microorganisms: from the screening of combinatorial libraries to live recombinant vaccines," *Nat. Biotechnol.*, 15:29-34, 1997.

(Continued)

*Primary Examiner*—S. Devi
(74) *Attorney, Agent, or Firm*—Fulbright & Jaworski L.L.P.

(57) ABSTRACT

A composition and method for treating a host having or at risk of infection by *Bacillus anthracis* using an affinity matured antibody or portion thereof derived from a monoclonal antibody.

16 Claims, 7 Drawing Sheets

OTHER PUBLICATIONS

Hayhurst and Georgiou,. "High throughput isolation," *Curr. Opin. Chem. Biol.*, 5:683-689, 2001.

Hayhurst and Harris, "*Escherichia coli* Skp chaperone coexpression improves solubility and phage display of single-chain antibody fragments," *Protein Expr. Purif.*, 15:336-343, 1999.

Hayhurst, "Improved expression characteristics of single-chain Fv fragments when fused downstream of the *Escherichia coli* maltose-binding protein or upstream of a single immunoglobulin-constant domain," *Protein Expr. Purif.*, 18:1-10, 2000.

Hoess, "Protein design and phage display," *Chem. Rev.*, 101:3205-3218, 2001.

Nosoh et al., *Protein Stability and Stabilization through Protein Engineering*, Chapter 7, p. 197, 1991.

Wittrup, "The single cell as a microplate well," *Nat. Biotechnol.*, 18:1039-1040, 2000.

Castillo et al., "T7 displayed peptides as targets for selecting peptide specific scFvs from M13 scFv display libraries," *J. Immunol. Methods*, 257:117-122, 2001.

Knappik et al., "Fully synthetic human combinatorial antibody libraries (HuCAL) based on modular consensus frameworks and CDRs randomizied with trinucleotides," *J. Mol. Biol.*, 296:57-86, 2000.

Stemmer, "Rapid evolution of a protein in vitro DNA shuffling," *Nature*, 370:389-391, 1994.

Walroy et al., "Comparison of four serological methods for the detection of diphtheria anti-toxin antibodies," *J. Immunol. Methods*, 245:55-65, 2000.

\* cited by examiner

FIG. 1

RECOMBINANT ANTIBODIES FOR THE DETECTION AND NEUTRALIZATION OF ANTHRAX TOXIN

This application is a conversion from and claims priority of U.S. Provisional Application No. 60/332,849, filed on Nov. 5, 2001.

This invention was made with government support under U.S. Army, U.T. Austin Acct. No. 26-0454-85 and under grant No. DAA21-93C-0101 awarded by the Department of Defense. The government has certain rights in the invention.

TECHNICAL FIELD OF THE INVENTION

The present invention relates generally to the field of antibody engineering and in particular to a neutralizing antibody construct with therapeutic utility in early and advanced stages of therapy.

BACKGROUND OF THE INVENTION

Without limiting the scope of the invention, its background is described in connection with the treatment of *Bacillus anthracis* infection, one of the first biological warfare agents to be developed and is now perceived as a major threat in the United States, as an example.

Heretofore, in this field, research on the spore forming bacterium *Bacillus anthracis* has been limited due to its rare occurrence in humans. Infections due to *Bacillus anthracis*, commonly referred to as anthrax, most commonly occur in hoofed mammals. In humans, the preventive treatment strategy is generally limited to the use of a few antibiotics, including penicillin, doxycycline and fluoroquinolones. (Morbidity and Mortality Weekly Report. 2001. Update: Investigation of bioterrorism-related anthrax and interim guidelines for clinical evaluation of persons with possible anthrax. 50:941-8) While an anthrax vaccine can also prevent infection, the Centers for Disease Control and Prevention (CDC) does not recommend widespread immunization for the general public. (CDC Health Alerts, Advisories, and Updates. 2001. CDC Interim Recommendations for protecting workers from exposure to *Bacillus anthracis* in work site where mail is handled or processed. Oct. 31, 2000 www.cdc.gov/DocumentsApp/Anthrax/10312001/han51.asp). In fact, vaccination for the general public is not available.

Serious forms of human anthrax include inhalation anthrax, cutaneous anthrax, and intestinal anthrax. Inhalation anthrax is usually fatal. The intestinal disease form of anthrax may follow the consumption of contaminated food and is characterized by an acute inflammation of the intestinal tract. Direct person-to-person spread of anthrax is extremely unlikely, if it occurs at all. Therefore, the CDC explains that there is no need to immunize or treat contacts of persons ill with anthrax, such as household contacts, friends, or co-workers, unless they also were also exposed to the same source of the infection.

For persons infected with anthrax, treatment success is limited by several factors, such as the increased incidence of antibiotic resistance and treatment delays that lessen the chance of survival. It is known that early treatment of anthrax with antibiotics is essential to reduce mortality-delays in treatment profoundly decrease survival rates. Early treatment, however, is difficult because initial symptoms of the infection, e.g., when the bacterial spores are inhaled, heretofore known as inhalation anthrax, may resemble those of the common cold. In addition, symptoms of anthrax infection, depending on how the bacterium is contracted, may take seven to sixty days to appear.

The pathogenicity of *B. anthracis* is expressed in two ways: a toxic effect made evident by the appearance of an edema, and a so-called lethal toxic effect that may lead to the death of the subject infected. These effects are attributed to the presence of toxins produced by a combination of three protein factors present in *B. anthracis*. In both humans and mammals, toxins will increase in the body even during early stages of infection when the host appears asymptomatic. This explains why delays in treatment can be fatal. Thus, there is not only a critical need for better anthrax intervention therapies, but a critical need for point-of-care, rapid, and extremely sensitive diagnostic tests to establish the presence of anthrax early in the infection.

Passive immunization in an effort to neutralize toxins with antibodies, usually polyclonal antibodies, has been used as a therapeutic intervention for a variety of bacterial infections (Keller M A, Stiehm E R, Passive Immunity in Prevention and Treatment of Infectious Diseases. *Clin. Microbiol. Reviews* 13: 602-614). A major limitation of using polyclonal antisera in patients is the possibility of "serum sickness" due to a patient's immune response to proteins derived from a different species. In addition, higher affinity antibodies are more effective for toxin neutralization, but there is no general way to enhance intentionally the affinity of polyclonal sera or even monoclonal antibodies derived from hybridomas.

A general therapeutic method for the neutralization of toxins using high affinity, engineered antibodies or antibody constructs could have application to a wide variety of bacterial infections including native bacterial strains that produce anthrax, diptheria, pertussis, tetanus, and *E. coli* strains producing Shiga toxin. Pathogenic bacteria of the Australia group such as *Brucella abortus, Brucella melitensis, Brucella suds, Chlamydia psittaci, Clostridium botulinum, Francisella tularensis, Pseudomonas mallet, Pseudomonas pseudomallei, Salmonella typhi, Shigella dysenteriae, Vibrio cholerae, Yersinia pestis* could also be considered for antibody intervention. In addition, genetically engineered pathogens intended for use as biowarfare agents containing introduced toxins such as Botulinum toxins, *Clostridium perfringens* toxins, Conotoxin, Ricin, Saxitoxin, Shiga toxin, *Staphylococcus aureus* toxins, Tetrodotoxin, Verotoxin, Microcystin (Cyanginosin), Abrin, Cholera toxin, Tetanus toxin, Trichothecene mycotoxins, or toxins derived from animal venoms could be neutralized in a similar fashion, leading to dramatically increased survival rates, even for infections in which no vaccine is available.

SUMMARY OF THE INVENTION

It has been found, however, that present compositions and methods for the prophylatic treatment of patients exposed to *Bacillus anthracis* fail to target the protective antigen or toxin of the bacterium in a manner that allows antibiotic treatment to have a full effect on infectious disease. A significant problem of current treatment regimes is that the antibodies fail to have the required affinity and avidity for widespread use.

What is needed is a purified affinity-matured recombinant antibody or portion thereof having binding specificity for the *Bacillus anthracis* protective antigen. In one embodiment the antibody is cloned from anti-protective antigen hybridoma, e.g., the mouse hybridoma 14B7. The antibody portion may be any portion or fragment of an antibody, e.g., an scFv fragment. The antibody may be of any antibody class. The antibody may be, e.g., derived from an scFv fragment further includes antibody constant regions to create monovalent antibody portion of, e.g., at least 40 kDa.

The antibody may be affinity matured by selecting for clones having higher affinity than the wild-type antibody sequence cloned from a hybridoma after imperfect PCR amplification, e.g., error-prone expression libraries. In one embodiment, the clones that exhibit at least three-fold higher affinity and an increased stability to the protective antigen than wild-type are selected.

The affinity matured antibodies or portions thereof may be fused to, e.g, a 14B7 wild type to create divalent homodimeric antibodies. The antibody or portions thereof will generally confer protection to a host against Bacillus anthracis toxin. The host may be, e.g., a human and exhibit, in one example, about a one-to-one stoichiometry. The purified antibody for the Bacillus anthracis protective antigen will exhibit generally an equilibrium dissociation constant of at least about 63 nM.

The present invention is also directed to a process for producing affinity matured antibodies to bacterial toxins that produce an immune response protective against the symptoms of bacterial infection. The process includes culturing a microorganism that expresses a bacterial toxin or fragments thereof in a bacteriophage that is expressed in the microorganism. Next, a bacteriophage library is expresses an affinity matured antibodies or portions thereof. The bacteriophage library and the microorganism are contacted and the bacteriophage with at least three-fold higher affinity to the bacterial toxin are selected. Using the present invention affinity matured antibodies were generated that are specific for a Bacillus anthracis protective antigen.

The present invention further includes a method of treating a host having or at risk of infection by Bacillus anthracis, the method comprising the step of administering to a host a composition comprising an affinity matured antibody or portion thereof derived from a monoclonal antibody. The affinity matured antibody may be administered after onset of symptoms or may be administered prophylactically. In one embodiment the affinity matured antibody or portion thereof may be an scFv fragment, e.g., having a dissociation constant of at least about 63 nM.

The present invention also includes a pharmaceutical composition for the treatment of a pathogenic infection including an affinity matured antibody or portion thereof against a toxin in a pharmaceutically acceptable carrier. The toxin may be a bacterial toxin, e.g., a Bacillus anthracis toxin. For example, a treatment for Bacillus anthracis infection may includes administering to an individual in need thereof a therapeutically effective amount of a purified affinity matured antibody or portion thereof having binding specificity for the Bacillus anthracis protective antigen in a pharmaceutically acceptable carrier.

The present invention also includes a diagnostic device that incorporates immobilizes an affinity-matured antibody having an a affinity for a proteinaceous toxin. The converse arrangement is also included, namely, where the proteinaceous toxin is immobilized and used to diagnose the presence of an affinity matured antibody.

The present invention also includes a diagnostic method for detecting exposure to a proteinaceous toxin made up of the steps of contacting a diagnostic device that includes incorporates immobilizes an affinity-matured antibody having an a affinity for a proteinaceous toxin, with a fluid such as blood or urine, and analyzing the diagnostic device.

BRIEF DESCRIPTION OF THE DRAWINGS

For a more complete understanding of the features and advantages of the present invention, reference is now made to the detailed description of the invention along with the accompanying figures in which corresponding numerals in the different figures refer to corresponding parts and in which:

FIG. 1 is a diagram that outlines the B. anthracis toxin mechanism;

DETAILED DESCRIPTION OF THE INVENTION

Figure 2:
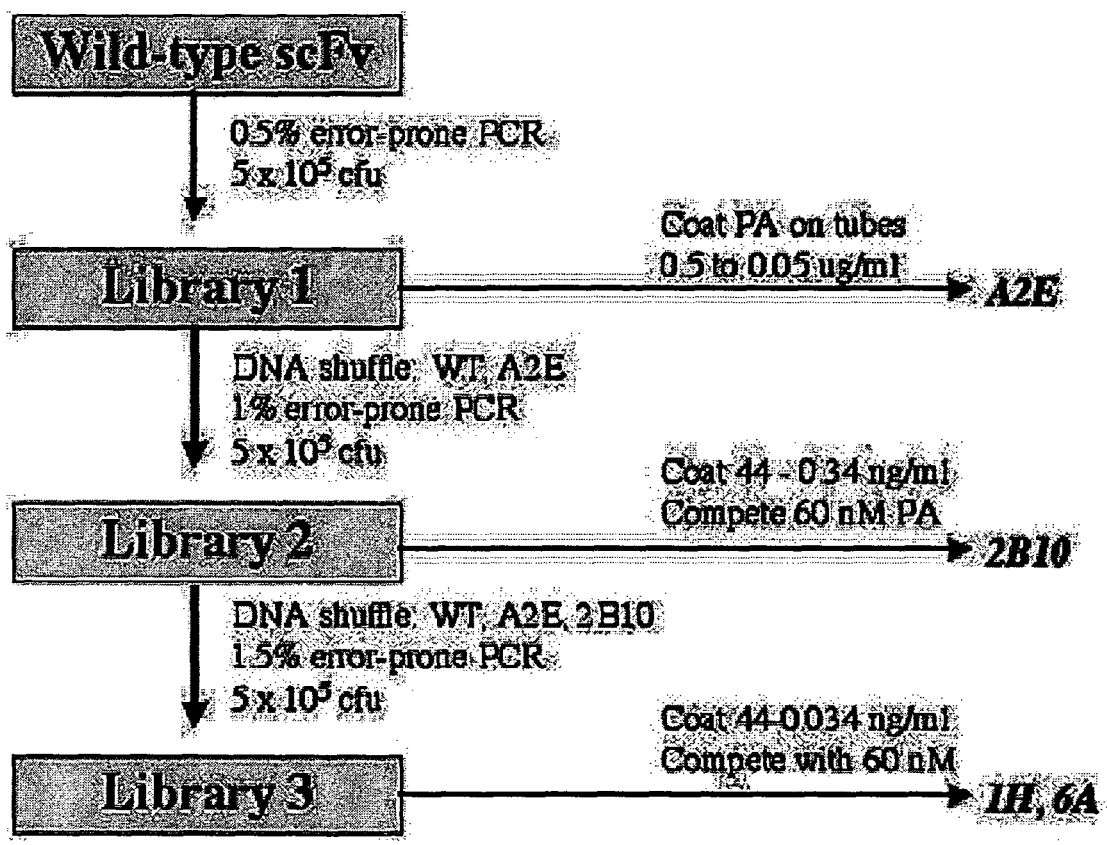
FIG. 2 is an affinity maturation strategy.

While the making and using of various embodiments of the present invention are discussed in detail below, it should be appreciated that the present invention provides many applicable inventive concepts that may be embodied in a wide variety of specific contexts. The specific embodiments discussed herein are merely illustrative of specific ways to make and use the invention and do not delimit the scope of the invention.

Anthrax is a zoonotic soil organism endemic to many parts of the world. Infection through the inhalation of the heat resistant spores of the Gram positive bacterium, B. anthracis, results in up to 80% mortality rate if left untreated (Shafazand. CHEST 116:1369-76). In fact, B. anthracis was one of the first biological warfare agents to be developed and continues to be perceived as a major threat. While vaccine strains have been developed, widespread use is neither available nor recommended by the CDC.

Figure 1:
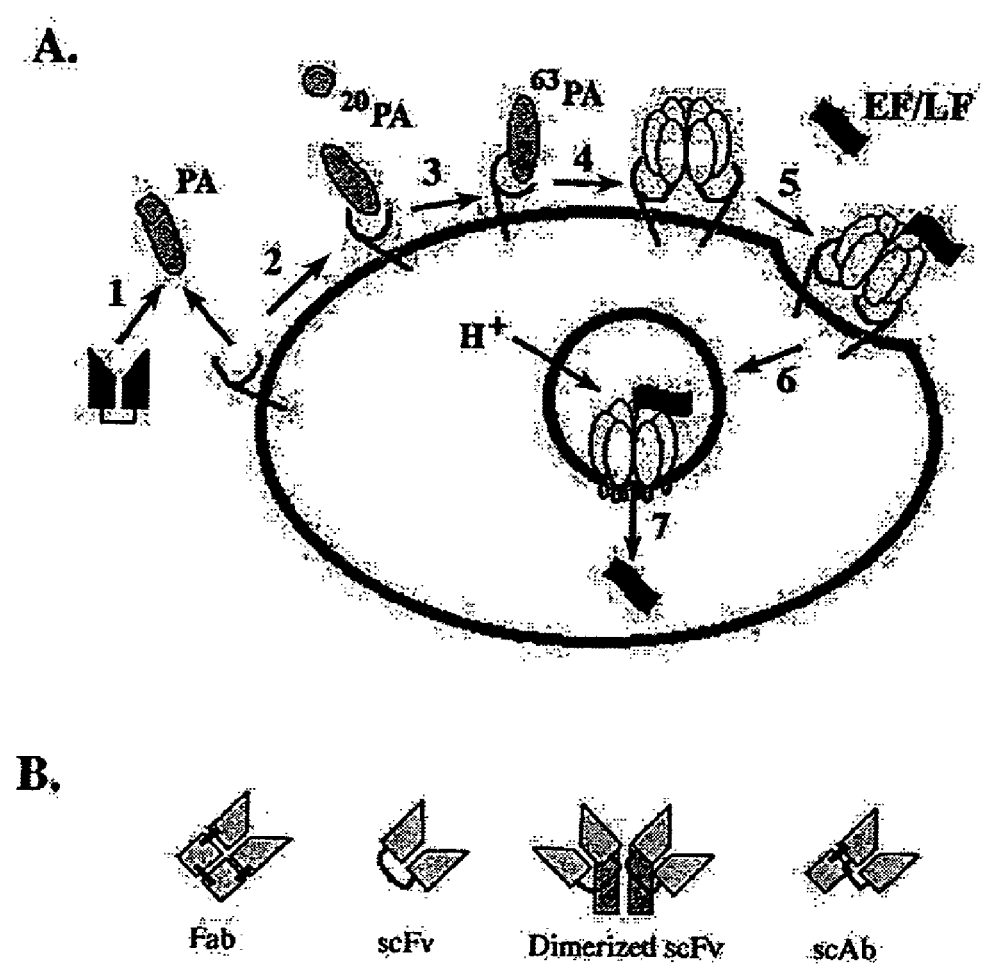

Following inhalation, the B. anthracis spores germinate in the alveolar macrophages and migrate to lymph nodes where they multiply and enter the bloodstream, quickly reaching $10^7$-$10^8$ organisms per milliliter of blood (Dixon T, Meselson M, Guillemin J, Hanna P. 1999. Anthrax. New England Journal of Medicine 341: 815-26). The vegetative bacteria excrete a tripartite exotoxin that is responsible for the etiology of the disease. The toxin is an 83 kDa polypeptide, protective antigen (PA), that binds to a recently identified receptor on the surface of macrophages (Bradley A B, Mogridge J, Mourez M, Collier R J, Young J A T. 2001. Identification of the Cellular Receptor for Anthrax Toxin. Nature 414:) and, following cleavage by a furin-like protease and oligomerization into a heptameric ring, facilitates translocation of the two catalytic components, the lethal factor (LF) or the edema factor (EF) (FIG. 1). LF is a zinc metalloprotease that cleaves MEK 1, 2, 3 leading to the release of cytokines TNFα and IL-1β and inducing shock in the host; EF is a calmodulin-dependent adenylate cyclase that causes local edema and impairs neutrophil function (Leppla. Handb Exp Pharmacol. 2000. 145:445-72).

Anthrax toxin mechanism and 14B7 neutralization steps are shown in FIG. 1A. In step 2, PA associates with an unidentified cellular receptor. PA is cleaved by a furin-like cell surface protease to release the 20 kDa N-terminal fragment, $^{20}$PA, in step 2; $^{63}$Pa remains bound. In step 4, receptor-bound PA heptamerizes, followed by EF and LF competitively binding heptamerized PA stoichiometrically in step 5. In step 6, the complex is internalized by receptor-mediated endocytosis followed by acidification of the vacuole, after which PA changes conformation creating a pore in the endo-lysosome membrane through which EF/LF diffuse as shown in step 7. The antibody 14B7 interfering with this process by competing, with the cellular receptor for the PA binding site in step 1. FIG. 1B illustrates the antibody constructs: Fab, generated from proteolytic digestion of intact antibody; monovalent scFv; scFv dimerized by C-terminal dimerization helices, and scAb generated by C-terminal fusions to an scFv of a human constant kappa domain.

Blocking the action of the toxin has been actively pursued as a therapeutic strategy for preventing mortality following challenge with toxin or with spores. Blocking the toxin is best accomplished by disrupting the function of PA in one of three ways: preventing the binding of the catalytic subunits with antibodies or peptides (Mourez M, Kane R S, Mogridge J, Metallo S, Deschatelets P, et al. 2001. Designing a polyvalent inhibitor of anthrax toxin. *Nature Biotechnology* 19: 958-61; Little S F, Novak J M, Lowe J R, Leppla S H, Singh Y, et al. 1996. Characterization of lethal factor binding and cell receptor binding domains of protective antigen of *Bacillus anthracis* using monoclonal antibodies. *Microbiology* 142: 707-15), interfering with PA oligomerization using negative dominant mutants (Sellman B, Mourez M, Collier R. 2001. Dominant-Negative Mutants of a Toxin Subunit: An Approach to Therapy of Anthrax. *Science* 292: 695-7; Singh Y, Khanna H, Chopra A, Mehra V. 2001. A dominant negative mutant of *Bacillus anthracis* protective antigen inhibits anthrax toxin in vivo. *Journal of Biological Chemistry* 276: 22090-4) or by blocking the binding of the toxin to its receptor with antibodies. The latter strategy has been investigated more extensively and is the only one to have been tested in experimental animals challenged with aerosolized anthrax spores (Little S, Ivins B, Fellows P, Friedlander A. 1997. Passive protection by polyclonal antibodies against *Bacillus anthracis* infection in guinea pigs. *Infection and Immunity* 65: 5171-5). The elicitation of polyclonal antibodies to PA correlate with protection (Pitt M, Little S, Ivins B, Fellows P, Barth J, et al. 2001. In vitro correlate of immunity in a rabbit model of inhalational anthrax. *Vaccine* 19: 4768-73) and in fact constitute a primary immunogenic component of the FDA-approved vaccine. The ability of monoclonal antibodies to protect against challenge, particularly to highly virulent strains of anthrax, is still in question (Little S, Ivins B, Fellows P, Friedlander A. 1997. Passive protection by polyclonal antibodies against *Bacillus anthracis* infection in guinea pigs. *Infection and Immunity* 65: 5171-5).

The key to effective toxin neutralization is high affinity, based on a slow kinetic off-rate. If the antibody off-rate is slower than the clearance time of the antibody-toxin complex in human sera, then the antibodies could effectively remove toxin stoichiometrically. Even if clearance rates are slower than antibody off-rates, it stands to reason that higher affinity antibodies will be better able to neutralize smaller amounts of a toxin. Thus, high affinity antibodies could be used at much lower doses, reducing the chance for side effects such as unwanted immune reactions to the antibody therapeutic reagent. Antibodies with dissociation constants ($K_D$) of about 70 nM or lower are required to neutralize potent toxins. Unfortunately, there is no way to enhance the affinities of antibodies from polyclonal immune sera or monoclonal antibodies derived from hybridomas. One must simply "take what one gets" following animal immunization. Antibody engineering, on the other hand, not only allows antibody affinity and specificity improvement through rational and evolutionary methods, the affinity and specificity enhanced antibodies can be produced in a variety of formats such as humanized whole IgG, Fab, scAb, and scFv using genetic engineering techniques. These different formats all have unique therapeutic advantages.

For all of the reasons outlined above, there is a need to alleviate the symptoms of anthrax and extend the window of time for antibiotic therapy following infection. The compositions and methods of this invention provide healthcare professionals and researchers with a unique therapy that confers increased protection of the infected person or mammal, heretofore known as a host, and for the first time treat patients at advanced stages of infection.

In general, the following words or phrases have the indicated definitions when used in the description, examples, and claims:

The term Fv is defined to be a covalently- or noncovalently-associated heavy and light chain heterodimer that does not contain constant domains. The term scFv refers to the single chain heterodimer.

The term Fab' is defined herein as a polypeptide comprising a heterodimer of the variable domain and the first constant domain of an antibody heavy chain, plus the variable domain and constant domain of an antibody light chain, plus at least one additional amino acid residue at the carboxy terminus of the heavy chain $C_H 1$ domain including one or more cysteine residues. F(ab')$_2$ antibody fragments are pairs of Fab' antibody fragments which are linked by a covalent bond(s). The Fab' heavy chain may include a hinge region. This may be any desired hinge amino acid sequence. Alternatively the hinge may be entirely omitted in favor of a single cysteine residue or, preferably a short (about 1-10 residues) cysteine-containing polypeptide. In certain applications, a common naturally occurring antibody hinge sequence (cysteine followed by two prolines and then another cysteine) is used; this sequence is found in the hinge of human IgG$_1$ molecules (Kabat E A, et al. 1987. Sequences of Proteins of Immunological Interest 3rd edition. National Institutes of Health, Bethesda, Md.). In other embodiments, the hinge region is selected from another desired antibody class or isotype. In certain preferred embodiments of this invention, the C-terminus of the $C_H 1$ of Fab' is fused to the sequence Cys X X. X preferably is Ala, although it may be any other residue such as Arg, Asp, or Pro. One or both X amino acid residues may be deleted.

The "hinge region" is the amino acid sequence located between $C_H 1$ and $C_H 2$ in native immunoglobulins or any sequence variant thereof. In the case of the humanized 4D5 antibody described infra, the hinge region is located between residues 224 (asp in . . . Cys Asp Lys . . . ) and 233 (Pro in . . . . Cys Pro Ala). Analogous regions of other immunoglobulins will be employed, although it will be understood that the size and sequence of the hinge region may vary widely. For example, the hinge region of a human IgG1 is only about 10 residues, whereas that of human IgG$_3$ is about 60 residues.

The term Fv-SH or Fab'-SH is defined herein as a Fv or Fab' polypeptide having a cystinyl free thiol. Preferably the free thiol is in the hinge region, with the light and heavy chain cysteine residues that ordinarily participate in inter-chain bonding being present in their native form. In the most preferred embodiments of this invention, the Fab'-SH polypeptide composition is free of heterogenous proteolytic degradation fragments and is substantially (greater than about 90 mole percent) free of Fab' fragments wherein heavy and light chains have been reduced or otherwise derivatized so as not to be present in their native state, e.g. by the formation of aberrant disulfides or sulfhydryl addition products.

A humanized antibody for the purposes herein is an immunoglobulin amino acid sequence variant or fragment thereof which is capable of binding to a predetermined antigen and which comprises a FR region having substantially the amino acid sequence of a human immunoglobulin and a CDR having substantially the amino acid sequence of a non-human immunoglobulin or a sequence engineered to bind to a preselected antigen.

The term "control sequences" refers to DNA sequences necessary for the expression of an operably linked coding sequence in a particular host organism. The control sequences that are suitable for prokaryotes, for example, include a promoter, optionally an operator sequence, a ribosome binding site, and transcriptional terminators. Particularly preferred are highly regulated inducible promoters that suppress Fab' polypeptide synthesis at levels below growth-inhibitory amounts while the cell culture is growing and maturing, for example, during the log phase.

Nucleic acid is "operably linked" when it is placed into a functional relationship with another nucleic acid sequence. For example, DNA for a presequence or secretory leader is operably linked to DNA for a polypeptide if it is expressed as e preprotein that participates in the secretion of the polypeptide; a promoter or enhancer is operably linked to a coding sequence if it effects the transcription of the sequence; or a ribosome binding site is operably linked to e coding sequence if it is positioned so as to facilitate translation. Generally, "operably linked" means that the DNA sequences being linked are contiguous and, in the case of a secretory leader, contiguous and in same reading frame. However enhancers do not have to be contiguous. Linking is accomplished by ligation at convenient restriction sites. If such sites do not exist, then synthetic oligonucleotide adaptors or linkers are used in accord with conventional practice.

An "exogenous" element is defined herein to mean a nucleic acid sequence that is foreign to the cell, or homologous to the cell but in a position within the host cell nucleic acid in which the element is ordinarily not found.

As used herein, the expressions "cell" and "cell culture" are used interchangeably end all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Different designations are will be clear from the contextually clear.

"Plasmids" are designated by a lower case p preceded and/or followed by capital letters and/or numbers. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., 1981. Nucleic Acids Res., 9:6103-6114, and Goeddel et al., 1980. Nucleic Acids Res. 8:4057.

"Preparation" of DNA from cells means isolating the plasmid DNA from a culture of the host cells. Commonly used methods for DNA preparation are the large and small scale plasmid preparations described in sections 1.25-1.33 of Sambrook et al. (Molecular Cloning: 1989. A Laboratory Manual New York: Cold Spring Harbor Laboratory Press). DNA preparations are purified by methods well known in the art (see section 1.40 of Sambrook et al., supra).

"Bacteriophage" is one or a number of virus for which the natural host is a bacterial cell.

As used herein, monoclonal antibodies are produced by hybridoma cells, which are fusions of antibody-producing cells and myeloma cells. Monoclonal antibodies are specific, can be directed against almost any antigen of interest, and can be produced in large amounts.

One form of the present invention includes a panel of anti-PA scFv antibodies exhibiting a range of equilibrium dissociation constants ($K_D$) between 63 nM and 0.25 nM as measured by surface plasmon resonance. The engineered scFv antibodies exhibit exceptional stability to incubation in serum and to urea and heat denaturation, parameters that affect the biodistribution of scFvs in vivo. Protection to anthrax toxin challenge in an in vitro cell culture assay as well as in a rat model correlated strongly with affinity with the highest affinity antibody (1H, $K_D$=0.25 nM) conferring maximal protection. Homodimeric, divalent variants of the scFvs are also prepared to evaluate the effect of avidity on protection. The higher avidity antibodies are highly effective in neutralizing the toxin in the cell culture assay but not in the rat model, perhaps due to their lower stability. Finally, scFvs fused to a human constant kappa domain (scAbs) is used to evaluate the effect of delayed clearance kinetics by the kidney (28 kDa for scFvs versus 45 kDa for scAbs).

With the present invention, other bacterial toxins such as pertussis toxin, Botulinum toxins, *Clostridium perfringens* toxins, Conotoxin, Ricin, Saxitoxin, Shiga toxin, *Staphylococcus aureus* toxins, Tetrodotoxin, Verotoxin, Microcystin (Cyanginosin), Abrin, Cholera toxin, Tetanus toxin, Trichothecene mycotoxins, or toxins derived from animal venoms are also neutralized using stepwise genetic engineering steps to create antibodies against the above-mentioned toxins.

A variety of antibody constructs have been used for therapeutic purposes. These include whole IgG antibodies, Fabs, scFvs and various dimer constructs such as scAbs. The larger constructs, especially the whole IgG antibodies have the considerable advantage of long serum residence time. The dimeric constructs have the advantage of avidity and the smaller constructs have the advantage of enhanced tissue penetration.

In addition to bacterial toxins, high affinity engineered antibodies could be especially important for neutralization of insect, mollusk, and reptile venoms following encounters with these animals. Smaller constructs such as high affinity scFv or scabs could be particularly effective here as the higher clearance rates would be an advantage since chances of obtaining serum sickness would be remote compared with whole IgG, and smaller constructs such as scFv can penetrate tissues more effectively than larger types of antibody constructs.

Antibodies with enhanced affinity also provide greater sensitivity as diagnostic reagents. This increase in sensitivity as a diagnostic reagent could make earlier diagnosis possible of systemic anthrax via identification of smaller amounts of anthrax toxin in the bloodstream. Earlier diagnosis, especially within hours at point of care, would make more likely a successful early therapeutic intervention.

It is also noteworthy that one of skill in the art will be able to use other antibodies to the anthrax PA toxin, such as 1G3, that bind to other areas of PA. Targeting toxins such as PA at several different epitopes may have certain therapeutic or diagnostic advantages, such as enabling a so-called "sandwich" assay format for a diagnostic test or providing synergistic, non-competitive reagents for therapeutic use.

EXAMPLES

Cloning from Hybridomas. The heavy and light variable chain regions are cloned from anti-PA hybridoma 14B7 via RT-PCR (Krebber A, Bornhauser S, Burmester J, Honegger A, Willuda J, et al. 1997. Reliable cloning of functional antibody variable domains from hybridomas and spleen cell repertoires employing a reengineered phage display system. *J Immunol Methods* 201: 35-55). $V_H$ and $V_L$ genes are joined by overlap PCR and cloned into pAK100 phage display vector using 5 prime and 3 prime SfiI sites. Single colonies in *E. coli* strain are grown in a 96-well plate, and phage displaying scFv are produced and screened by ELISA to identify PA-reactive clones.

Antibody Affinity Maturation. Error-prone libraries of the 14B7 scFv gene are constructed using manganese and biased nucleotide ratios (Daugherty P, Chen G, Iverson B, Georgiou G. 2000. Quantitative analysis of the effect of the mutation frequency on the affinity maturation of antibodies. *Proc Natl Acad Sci USA In press*). DNA shuffling is performed as described (Stemmer W P C. 1994. Rapid evolution of a protein in vitro by DNA shuffling. *Nature* 370: 389-91). The library construction and screening strategies and the lineage of affinity-improved clones are described in FIG. 2, in which error prone PCR and DNA shuffling are performed. For example, panning is performed by coating immunotubes (Nunc) or high binding ELISA wells (Costar) with decreasing concentrations of PA (0.05 µg/ml to 0.0003 pg/ml) overnight, blocking with 5% milk-PBS, adding $10^{11}$-$10^{12}$ pfu phage for one hour, followed by addition of soluble PA to bind low affinity phage (60 nM) for two hours. After washing (20 times with PBS containing 0.1% TWEEN-20 followed by 20 washes with PBS), phage are eluted with 1 ml 0.1 M ethanolamine for 10 minutes, transferred to new tubes and neutralized with 500 µl 1M Tris-HCl, pH 7.5. Eluted phage is titered and used to infect exponentially growing TG1 cells for the next round of panning. Each library is panned for five rounds before screening for affinity matured variants.

Figure 3:
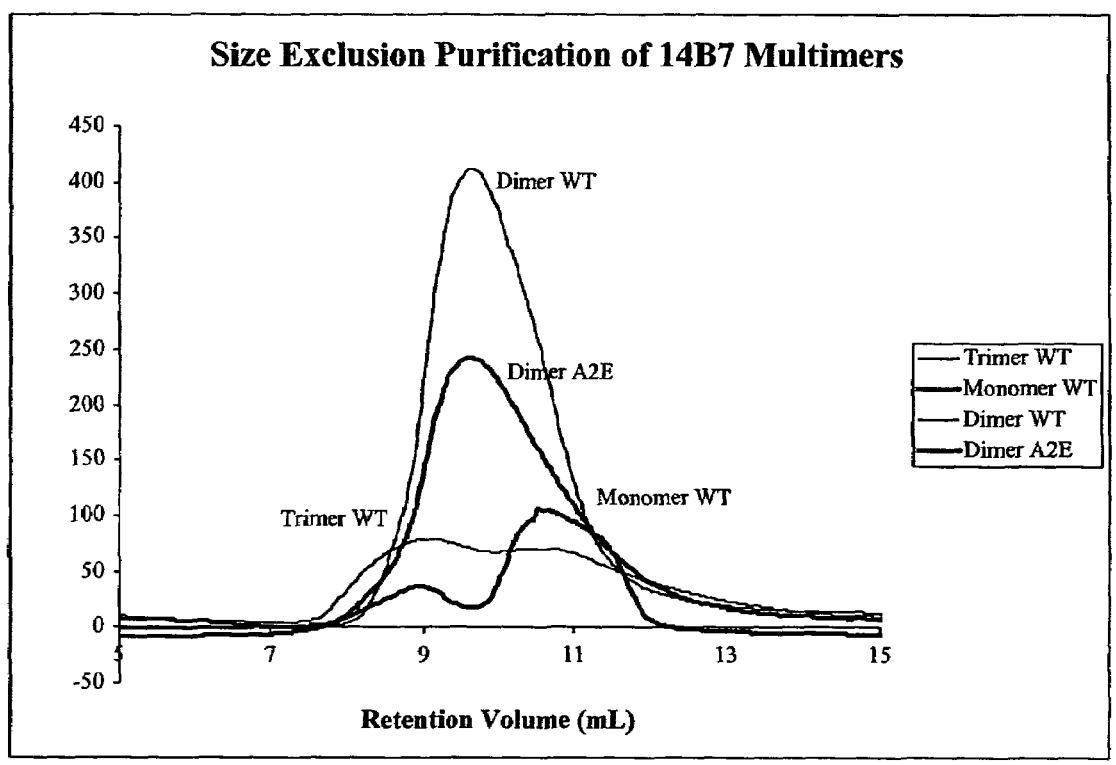
FIG. 3 is an FPLC analysis of antibody constructs.

Antibody Expression. scFvs is subcloned from the phage display vector pAK100 via SfiI-SfiI into the expression vectors in one of three ways: (a) pAK300 for scFv expression; (b) pAK500 to generate di-valent antibodies consisting of scFvs fused to a C-terminal dimerizing peptide (Krebber A, Bornhauser S, Burmester J, Honegger A, Willuda J, et al. 1997. Reliable cloning of functional antibody variable domains from hybridomas and spleen cell repertoires employing a reengineered phage display system. *J Immunol Methods* 201: 35-55); or (c) pMOPAC16, a pAK400 derivative for scAb expression (scFv with a C-terminal human constant kappa domain fusion) and co-expressing the periplasmic chaperone, skp. Proteins are produced in the periplasm of *E. coli* strain BL21, and purified by osmotic shock and immobilized metal affinity chromatography (Amersham Pharmacia) (Hayhurst A, Harris W J. 1999. *Escherichia coli* skp chaperone coexpression improves solubility and phage display of single-chain antibody fragments. *Protein Expr Purif* 15: 336-43). Mono- and dimeric scFv and scAb proteins were resolved from forms with different oligomerization states by size exclusion chromatography (SUPERDEX-75, Amersham Pharmacia) with PBS as eluant (FIG. 3). For example, in FIG. 3, the eluant from the nickel affinity resin is loaded onto a SUPERDEX-75 column (Amersham Pharmacia) and eluted with PBS. The scFv eluted primarily as a monomer with about 20% as dimers and higher M.W. aggregates. Following re-chromatography under identical conditions the monomer is eluted as a single peak. The divalent Fv construct appears as homogenous both on the basis of the elution profile and by native PAGE analysis. Purified yields are approximately 200 ng/$OD_{600}$ which is equivalent to 1 ug/ml for all scFv variants. Levels of contaminating endotoxin is measured by the LAL endotoxin test and are found to be <10 ng/L for all preparations. Protein concentrations are measured by micro-BCA assay as apparent to those in the art of microbiology.

Preparation of Monoclonal Antibody and Fab Fragments. Ascites fluid is prepared from the mouse $IgG_1$ 14B7 hybridoma. IgG is precipitated with ammonium sulfate and purified by Protein G chromatography. Upon elution, the IgG fraction is concentrated to 10 mg/ml and desalted using a CENTRICON-30 column. Fab fragments are prepared by overnight digestion at 37° C. with papain (10 µg papain/mg immunoglobulin in PBS-1 mM EDTA-20 mM cysteine). The digested sample is diluted 10-fold in protein A binding buffer (1.5 M Glycine, 3 M NaCl, pH 8.9) and applied to a recombinant protein A column (Sigma). The flowthrough containing the Fab fragments is collected, concentrated to 2 mg/ml with a CENTRICON-10 column and applied to a size exclusion column (SUPERDEX-200, AmershamPharmacia) with PBS as eluant. The absence of contaminating Fc and intact IgG in the Fab fraction is confirmed by ELISA and SDS-PAGE.

Antibody: Antigen Binding and Stability Analysis. The analysis of antigen binding kinetics by surface plasmon resonance is performed [Chen et al. 2001]. Briefly, antigen (PA or BSA control) is immobilized on a CM5 chip (Pharmacia) at a level of approximately 1000 RUs. To diminish rebinding effects, samples are run at high flow rate (60 µl/min) in HBS buffer (10 mM HEPES, 3.4 mM EDTA, 150 mM NaCl, 0.005% P20 surfactant, pH 7.4). On-rates were determined using at least five concentrations of antibody, ranging between 25 and 300 nM.

Antibody stability at 37° C., 70° C. and at 4° C., as a control, is determined by incubating quadruplicate samples (16 µg/ml protein in PBS) at the respective temperatures and monitoring the amount of active antibody remaining by ELISA. Urea denaturation curves are obtained by diluting proteins to a final concentration of 16 µg/ml in PBS in the presence of urea concentrations varying from 0 to 8.7 M. After allowing the folded and unfolded proteins to equilibrate for 3 hours at room temperature, fluorescence emission spectra are obtained using a Photon Technology International spectrofluorimeter. The fluorescence maximum shifts from 330 nm in zero denaturant to 350 nm in 8.7 M denaturant, concomitant with a 42% increase in fluorescence intensity. Data represents the average of at least three measurements, and are analyzed (Pace C N. 1990. Measuring and increasing protein stability. *Trends in Biotechnology* 8: 93-8; Pace C, Shirley B, Thomson J. 1989. In *Measuring the Conformational Stability of a Protein*, ed. T. Creighton, pp. 311-30. New York: IRL). The reversibility of urea denaturation is evaluated and data are reported only for proteins that exhibited a fully reversible transition.

Protection of Mouse Macrophages to Toxin Challenge. Survival of RAW 264.7 mouse macrophage-like cells (ATCC #TIB-71) following administration of antibodies at specified times after challenge with toxin (post-challenge neutralization; 100 ng/ml PA, 50 ng/ml LF) is determined essentially as described by Little et al. (Little S F, Leppla S H, Cora E. 1988. Production and characterization of monoclonal antibodies to the protective antigen component of *Bacillus anthracis* toxin. *Infect Immun* 56: 1807-13) except that antibodies were added 0, 5, 10 or 20 minutes after challenge. After 3 hours, viability was monitored with MTT, and absorbance detected at $A_{590}$. The percent of cells surviving toxin challenge at a specified antibody dose is reported.

Protection Against Toxin Challenge in the Rat Model. In vivo neutralization experiments are performed essentially as described (Ivins B, Ristroph J, Nelson G. 1989. Influence of Body Weight on Response of Fischer 344 Rats to Anthrax Lethal Toxin. *Applied and Environmental Microbiology* 55: 2098-100). Fischer 344 rats (250-275 g each; mean, standard deviation to be added) are anesthetized by intra-peritoneal injection of 80 mg/kg weight ketamine and 10 mg/kg xylazine. Antibodies (or sterile PBS) are administered in a 200 μl volume in a blind study, followed after 5 minutes by a 10× MLD lethal dose of anthrax toxin (40 μg PA, 8 μg LF) (Ezzell J W, Ivins B E, Leppla S H. 1984. Immunoelectrophoretic analysis, toxicity, and kinetics of in vitro production of the protective antigen and lethal factor components of *Bacillus anthracis* toxin. *Infect Immun* 45: 761-7) in a 200 μl volume, both via penile vein injection. Five animals are used for each test condition, and are monitored for discomfort and time of death versus survival. Rats are maintained under anesthesia for 5 hours or until death to minimize discomfort. Death is monitored by a cessation of breathing and heart beat. Surviving rats are euthanized by overdose of sodium phenobarbitol by intra-peritoneal injection, followed by appropriate disposal. The protective ability of antibody preparations is measured as a delayed time to death, and is considered significant at the p<0.05 level as determined by Student's one tailed t-test.

Engineering of anti-PA Antibodies With Different Binding Affinities. The $V_H$ and $V_L$ genes of the 14B7 monoclonal antibody (Little S F, Leppla S H, Cora E. 1988. Production and characterization of monoclonal antibodies to the protective antigen component of *Bacillus anthracis* toxin. *Infect Immun* 56: 1807-13) are isolated by RT-PCR. Overlap extension PCR is used to produce a 750 bp scFv gene fragment with a sequence encoding a $(Gly_4Ser)_4$ linker inserted between the heavy and light chain sequences. The scFv gene is fused to pIII for display in filamentous bacteriophage. Error prone PCR is used to construct a library of $5 \times 10^5$ independent transformants which upon screening by phage display leads to the isolation of clone A2E. The corresponding scFv protein exhibits a three-fold higher affinity to PA, and markedly increased stability. DNA sequencing revealed that A2E contains a single L56Ser:Pro substitution in CDR L2 (Table 1).

TABLE 1

Summary of antibody affinity and stability

| | $k_{on}$ (× 10$^5$ M$^{-1}$ sec$^{-1}$) | $k_{off}$ (× 10$^{-4}$ sec$^{-1}$) | $K_d$ (nM) | 37° C. in serum | 70° C. stability* |
|---|---|---|---|---|---|
| 14B7 mAb | 5 | 13.5 ± 1.2 | 2.3 | 100% | 15% |
| Fab | 3 | 33 ± 2 | 12 | 100% | 100% |
| WT scFv | 3.1 ± 0.4 | 32 ± 2 | 12 | 100% | 3.5% |
| L97 scFv | 3 | 190 ± 20 | 63 | 100% | 10% |
| A2E scFv | 3 | 10 ± | 4.0 | 100% | 28% |
| 1H scFv | 7.2 ± 0.8 | 1.7 ± 0.2 | 0.24 | 100% | 5% |
| WT dimer | 6.2 ± 0.7 | 3.9 ± 1.3 | | 100% | 0.4% |
| 1H dimer | 6 | | | ND | 0.2% |
| WT scAb | 2.9 ± 0.3 | 30 ± 0.8 | | ND | 14% |
| 1H scAb | ND | ND | | ND | 10% |

$^\$$37° c. tests performed in 90% FBS for seven days.,
*Amount of PA binding remaining after 2 hours of incubation in PBS at 70° C.

Figure 4:
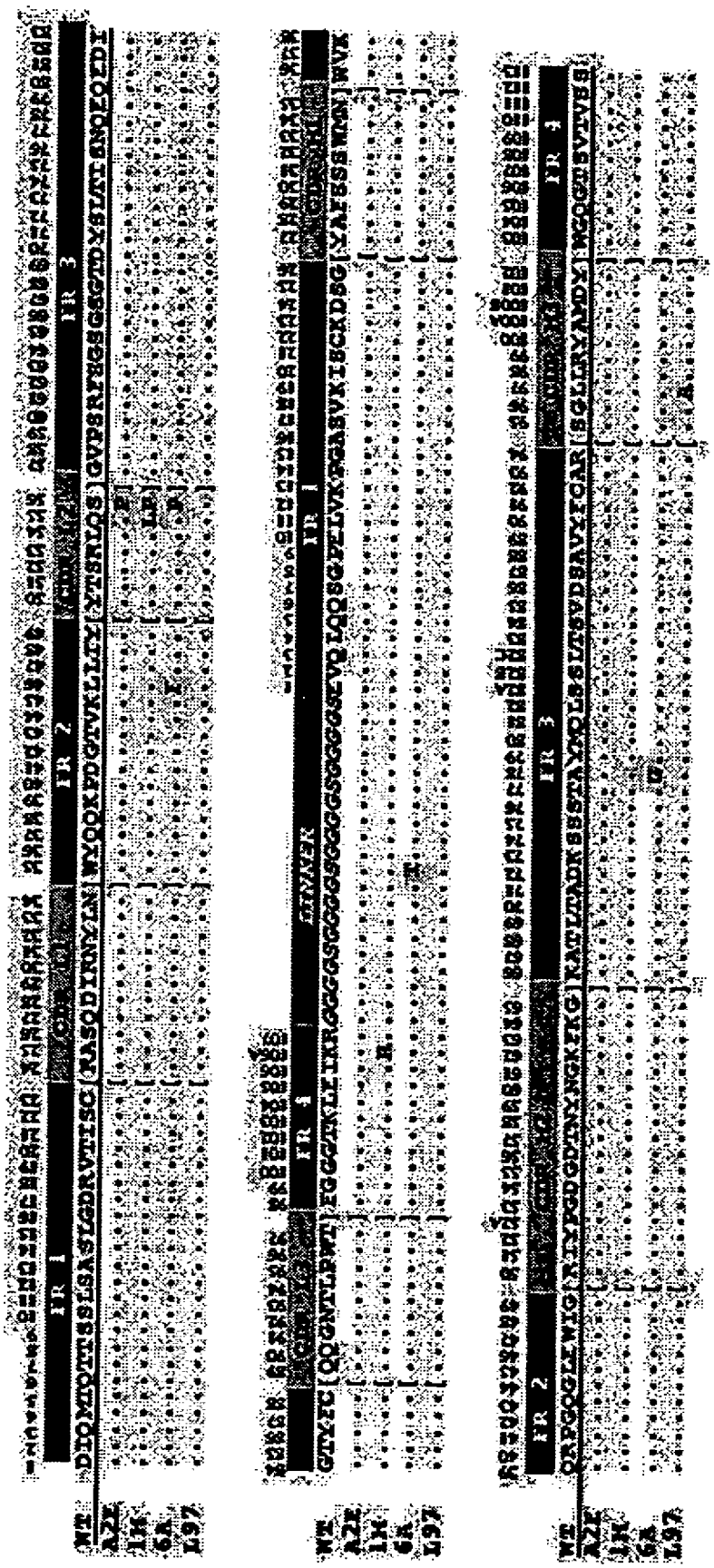
FIG. 4 is an amino acid sequence alignment of 14B7 scFv and related variants (SEQ ID NOS:1-5).

FIG. 4, shows the amino acid sequence alignment of 14B7 scFv and related variants. In FIG. 4, 14B7 WT sequence is written in single letter amino acid code. Kabat numbering scheme is indicated along side; CDRs are bracketed; and amino acid changes are indicated by red letters. The single L56Ser:Pro substitution in CDR L2 is present in all subsequent, higher affinity scFvs, even after backcrossing with the parental 14B7 scFv via DNA shuffling (Stemmer W P C. 1994. Rapid evolution of a protein in vitro by DNA shuffling. *Nature* 370: 389-91). For example, DNA shuffling of clones isolated from the fifth round of phage panning of the original library are then recombined by DNA shuffling. The resulting gene pool is amplified, subjected to random mutagenesis and screened by five rounds of phage panning. The entire process, i.e. shuffling, error prone mutagenesis and panning is repeated, giving rise to clones 6A and 1H that exhibit comparable antigen affinities. The latter antibody is selected for further studies. DNA sequencing reveals that 1H contains, in addition to L56Ser:Pro, two more mutations: L55Q:Leu in CDR L2 and H106ALys:Arg mutation located in heavy chain framework 4.

In addition to the affinity matured mutants, an antibody containing the mutation L97Leu:Ala is also constructed. The L97Leu:Ala substitution results in a higher equilibrium dissociation constant and is identified as part of an alanine scanning mutagenesis study of 33 residues at the 14B7:PA interface. Divalent, homodimeric scFv antibodies are constructed with by fusing the 14B7 wild type and the A2E and 1H scFvs with a C-terminal dimerization polypeptide (Krebber A, Bornhauser S, Burmester J, Honegger A, Willuda J, et al. 1997. Reliable cloning of functional antibody variable domains from hybridomas and spleen cell repertoires employing a reengineered phage display system. *J Immunol Methods* 201: 35-55). Finally, larger molecular weight monovalent scAbs (45 kDa) are generated by C-terminal fusion of the scFv to a human constant kappa domain (Hayhurst A, Harris W J. 1999. *Escherichia coli* skp chaperone coexpression improves solubility and phage display of single-chain antibody fragments. *Protein Expr Purif* 15: 336-43).

Figure 5:
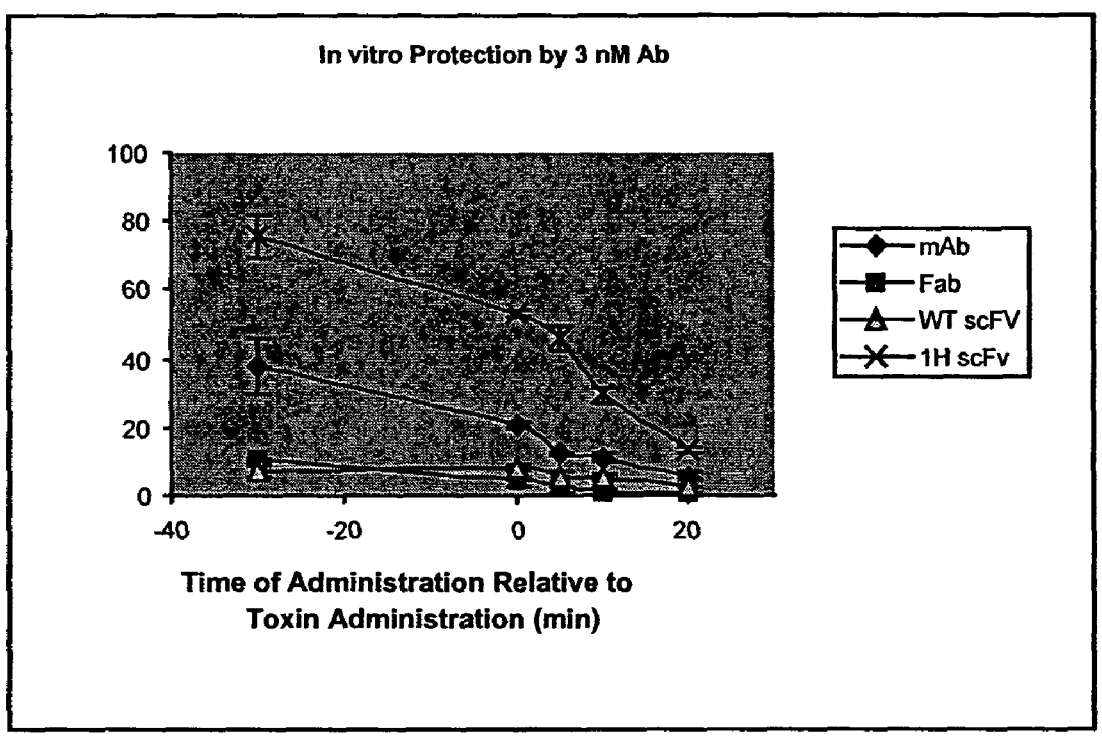
FIG. 5 is a graph showing in vivo post-challenge results.

Characterization. All the scFvs and scAbs are expressed in *E. coli* at a comparable level. Purified yields of at least between 0.25-0.5 μg protein/$A_{600}$ or 1 mg/L culture are obtained, comparable to those of other well expressed therapeutic scFv antibodies. The antibodies are purified by metal affinity chromatography followed by size exclusion FPLC to remove higher molecular weight aggregates. The scFvs are predominantly (>80%) monomeric indicating minimal tendency to dimerize in vivo during expression in *E. coli* (FIG. 5). Following chromatography, the isolated monomeric scFv proteins are >95% free of higher M.W. species. Freshly prepared antibody samples are used to determine antigen binding kinetics by surface plasmon resonance and for evaluating efficacy in neutralizing the anthrax toxin. The dimeric scFvs remained homogenous without the appearance of any contaminating lower- or higher molecular weight forms even after many weeks of incubation at 4° C.

The 14B7 Fab and the scFv exhibited identical antigen binding kinetics, as determined by surface plasmon resonance, a $k_{on}$ of $3.1 \pm 0.3 \times 10^5$ M$^{-1}$ sec$^{-1}$, and an off-rate of $0.0035 \pm 2$ sec$^{-1}$ giving an equilibrium dissociation constant of 12 nM (Table 1). For comparison, the divalent IgG exhibited a $K_D$ of 2.3 nM (measured under conditions of low coupling density of PA on the chip to minimize divalent binding). The A2E and 1H mutants exhibited, respectively 3-fold and 48-fold lower equilibrium dissociation constants (Table 1). In contrast the alanine mutant L97 exhibits $K_D$ that is over 5-fold higher than that of 14B7. Dimerization of the scFvs resulted in roughly ten-fold higher apparent affinities relative to the corresponding monomers. The increased affinity of the bivalent constructs is evidently due to avidity effects consistent with earlier findings (Willuda J, Kubetzko S, Waibel R, Schubiger P, Zangemeister-Wittke U, et al. 2001. Tumor targeting of mono-, di-, and tetravalent anti-p185HER2 miniantibodies multimerized by self associating peptides. *Journal of Biological Chemistry* 276: 14385-92).

Biodistribution and targeting efficiency of scFv antibodies that recognizes the epithelial tumor antigen glycocoprotein-2 correlate with the thermal and denaturant stability of the protein (e.g., Willuda J, Kubetzko S, Waibel R, Schubiger P, Zangemeister-Wittke U, et al. 2001. Tumor targeting of mono-, di-, and tetravalent anti-p185HER2 miniantibodies multimerized by self associating peptides. *Journal of Biological Chemistry* 276: 14385-92). Thus, differences in stability will mask the effect of affinity when evaluating the neutralizing potential of the anti-PA antibodies. Although most scFvs lose activity rapidly in serum at 37° C. (Benhar I, Pastan I. 1995. Identification of residues that stabilize the single-chain Fv of monoclonal antibodies B3. *J Biol Chem* 270: 23373-80; Helfrich W, Kroesen B J, Roovers R C, Westers L, Molema G, et al. 1998. Construction and characterization of a bispecific diabody for retargeting T cells to human carcinomas. *Int J Cancer* 76: 232-9), all the recombinant antibodies studied are found to be remarkable stable to deactivation in serum. The scFvs and the scAbs but not the dimerized scFvs also exhibited good stability at elevated temperatures (Table 1). Notably, the A2E scFv retained about 25% of its binding activity even after a 2 hour incubation at 70 C. The scAbs exhibit higher thermal stability than the respective scFv presumably due to the contribution of favorable interactions by the Ck domain. Remarkably, the 14B7 Fab exhibits no loss in binding activity under these conditions (Table 1).

Figure 6:
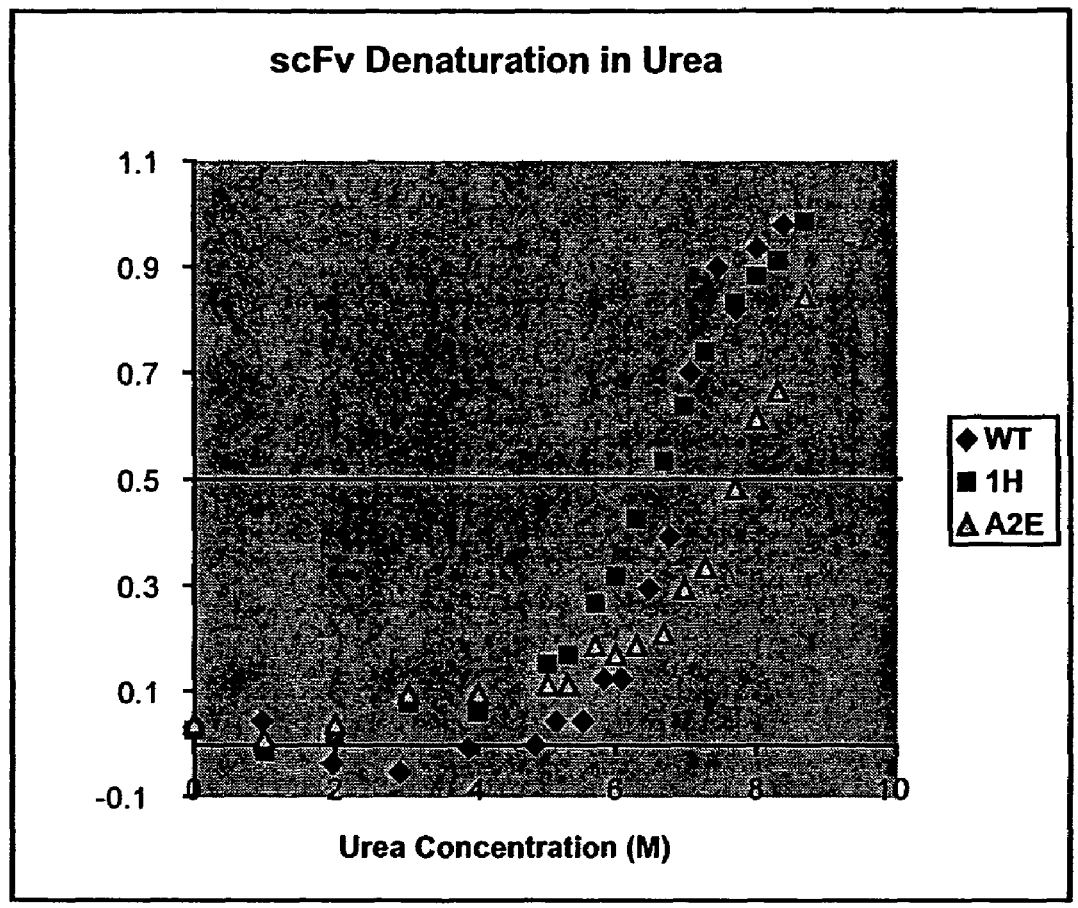
FIG. 6 is a graph that shows urea denaturation curves for 14B7 and affinity improved mutants.
Figure 7A:
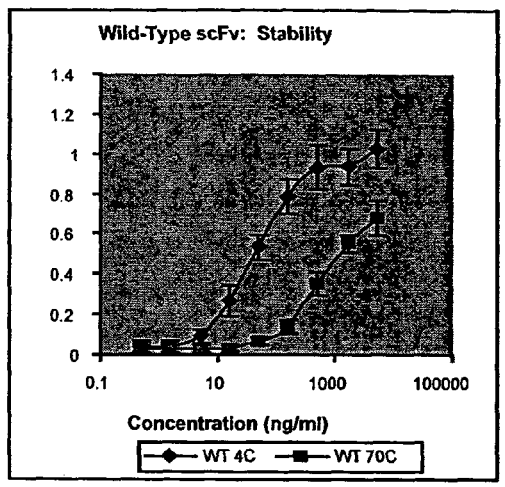
FIGS. 7A-7D are ELISA measurements of scFv monomer stability.
Figure 7B:
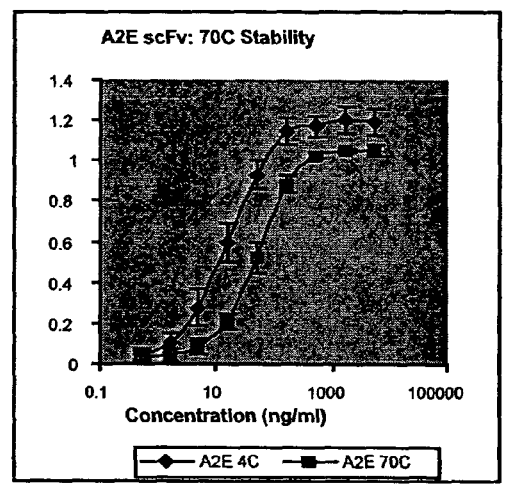
Figure 7C:
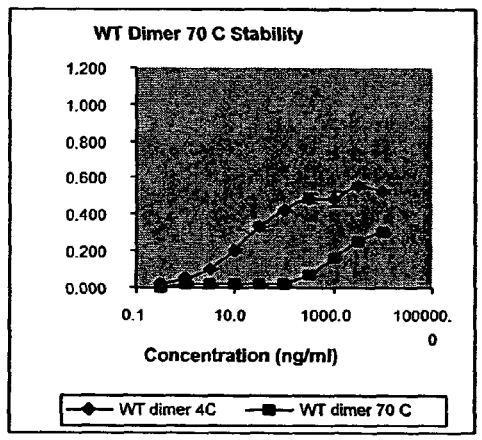
Figure 7D:
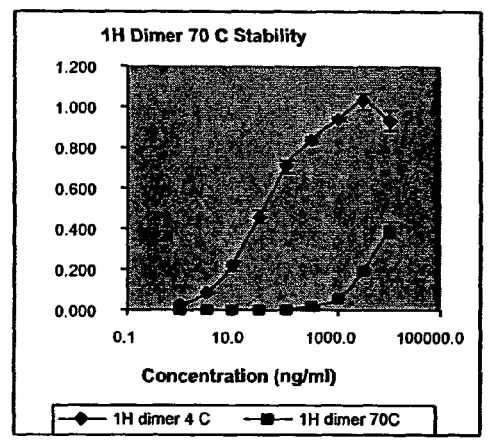

The denaturation of the antibodies in urea is evaluated by monitoring changes in protein fluorescence occurring upon unfolding (Pace C N. 1990. Measuring and increasing protein stability. *Trends in Biotechnology* 8: 93-8; Worn A, Pluckthun A. 2001. Stability Engineering of Antibody Single Chain Fv Fragments. *Journal of Molecular Biology* 305: 989-1010). The unfolding curves are shown to be fully reversible and the protein fluorescence upon dilution or dialysis from a high urea concentration was identical to that of proteins diluted directly to the same final urea concentration. In analogy with several other scFv antibodies, the anti-PA scFvs exhibit a relatively broad unfolding transition indicting that a simple two-stage model may not the suitable for describing the unfolding process, consistent with earlier studies (Worn A, Pluckthun A. 2001. Stability Engineering of Antibody Single Chain Fv Fragments. *Journal of Molecular Biology* 305: 989-1010). Notably, the A2E and 1H variants (both of which contain a Ser to Pro substitution) exhibit a broader transition region compared to the 14B7 scFv, most likely because the proline residue increases the heterogeneity of the denatured state. For all the scFvs, unfolding is detected only at urea concentrations above 5 M. The urea concentrations values for 50% unfolding ($m_{1/2}$ values) are 6.8, 7.7 and 6.5 M for the 14B7, A2E and 1H scFvs respectively (FIG. 6). For comparison, typical scFvs exhibit $m_{1/2}$ values between 2.5-4.5 M urea.

ELISA measurement of scFv monomer stability after 2 hour incubation at 4° C. or 70° C. is demonstrated in FIG. 7. Based on the concentration resulting in 50% of maximum signal, incubation at high temperature reduces WT to 3.5% of its previous activity; while variant A2E retains 25% of its activity. Results are average of quadruplicates (standard error indicated by error bars), significant to the $p<0.005$ level by a one-tailed t-test. See Table 1 for a complete listing of variants and their high temperature stability.

Toxin Neutralization. Protection of macrophages by antibodies administered at different times following toxin challenge is evaluated. Post-challenge protection correlated strongly with increased affinity (Table 2).

TABLE 2

Protection to challenge with toxin in the rat model

| Variable | Treatment | Dose (µg) | Dose (nmoles) | Time to Death (min)* | Number Survivors | Significance (t-test) |
|---|---|---|---|---|---|---|
| | PA Control | 40 | 0.5 | — | — | — |
| | LF | 8 | 0.1 | — | — | — |
| | PBS | — | — | 91 ± 7 | 0/5 | — |
| Affinity | L97 scFv | 56 | 2.0 | | | |
| | WT scFv | 56 | 2.0 | 110 ± 17 | 0/5 | <0.05 |
| | A2E scFv | 56 | 2.0 | 237 ± 63 | 2/5 | <0.05 |
| | 1H scFv | 56 | 2.0 | | 3/5 | |
| Size | Fab | 100 | 2.0 | 116* | 4/5 | |
| | 1H dimer scFv | 130 | 2.0 | 165 ± 11 | 2/5 | |
| | WT scAb | 90 | 2.0 | | | |
| | 1H scAb | 90 | 2.0 | | | |
| | 1H scAb | 22.5 | 0.5 | | | |

*Time to death calculated only for those animals who died during the five hour study period; all animal sacrificed after 5 hours.

∞Control animals sacrificed 30 minutes after PBS-treated animals expired.

Interestingly, the 14B7 scFv is significantly more effective relative to the 14B7 monoclonal resulting in lower $IC_{50}$ dosage. For example, when toxin and 3 nM antibody are administered at the same time (i.e. at t=0) the IC50 of the high affinity antibody 1H was 6-fold and 9-fold lower compared to the values obtained with the scFv and the monoclonal IgG, respectively. 1H conferred significant protection even 20 minutes post challenge while the parental scFv and the monoclonal did not. Overall, these results indicate that the smaller size of the scFv may be less effective in competing with the macrophage receptor for toxin binding.

Protection to toxin intoxication is examined in the Fisher 344 rat model. Rats are challenged with a 10×MLD amount of PA and LF (0.160 and 0.064 mg/kg respectively) and survival is monitored for five hours. Control rats receiving PBS only as treatment expired after 91±7 minutes. Animals receiving 14B7 scFv 5 minutes after toxin challenge exhibit a small but significant increase in time to death (110±17 minutes, p<0.05). Administration of the A2E scFv results in more dramatic delays in both the onset of symptoms and time to death (mean TTD 237±63 minutes with two survivors).

While this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

All publications and references mentioned in the specification are indicative of the level of skill of those skilled in the art to which this invention pertains. All publications and patent applications are herein incorporated by reference to the same extent as if each individual publication or reference was specifically and individually indicated to be incorporated by reference.

What is claimed is:

1. A purified affinity-matured antibody or a portion thereof having binding specificity for 83 kDa protective antigen (PA83) of *Bacillus anthracis*, wherein the affinity-matured antibody or the portion thereof exhibits an equilibrium dissociation constant of between 12 nM and 0.25 nM as measured by surface plasmon resonance, and wherein the affinity-matured antibody or the portion thereof confers protection to a host against a tripartite toxin of *Bacillus anthracis*.

2. The antibody of claim 1, wherein the antibody is affinity-matured from an antibody sequence cloned from an anti-*Bacillus anthracis* PA83 hybridoma.

3. The antibody of claim 1, wherein the antibody is affinity-matured from an antibody sequence cloned from the 14B7 anti-*Bacillus anthracis* PA83 hybridoma.

4. The antibody of claim 1, wherein the portion comprises an scFv fragment.

5. The antibody of claim 1, wherein the portion comprises an scFv fragment which further includes antibody constant regions to create a monovalent antibody portion of at least 40 kDa.

6. The antibody of claim 1, wherein the antibody is expressed in bacteria.

7. The antibody of claim 1, wherein the antibody exhibits an increased stability over a wild-type antibody sequence cloned from the 14B7 anti-*Bacillus anthracis* PA83 hybridoma.

8. The antibody of claim 1, wherein the antibody is expressed by a gene that is fused to a wild-type antibody coding sequence cloned from the 14B7 anti-*Bacillus anthracis* PA83 hybridoma.

9. The antibody of claim 1, wherein the host is a human.

10. The antibody of claim 1, wherein the host is a mammal.

11. The antibody of claim 1, wherein the antibody binds to the *Bacillus anthracis* PA83 with a one-to-one stoichiometry.

12. The antibody of claim 1, wherein the antibody alleviates symptoms of *Bacillus anthracis* toxin intoxication.

13. The antibody of claim 1, wherein the antibody neutralizes said *Bacillus anthracis* toxin.

14. The antibody of claim 1, wherein the antibody protects said host against *Bacillus anthracis* toxin poisoning.

15. A purified affinity-matured antibody or a portion thereof having binding specificity for 83 kDa protective antigen (PA83) of *Bacillus anthracis*, wherein the affinity-matured antibody or the portion thereof exhibits an equilibrium dissociation constant of between 4 nM and 0.25 nM as measured by surface plasmon resonance, and wherein the affinity-matured antibody or the portion thereof confers protection to a host against a tripartite toxin of *Bacillus anthracis*.

16. A purified affinity matured scFv comprising SEQ ID NO: 3.

* * * * *

SEQUENCE LISTING

<160> NUMBER OF SEQ ID NOS: 5

<210> SEQ ID NO 1
<211> LENGTH: 248
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 1

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu Gln Ser Gly Val Pro Ser Arg Phe Ser Gly
50                  55                  60

Ser Gly Ser Gly Thr Asp Tyr Ser Leu Thr Ile Ser Asn Gln Glu Gln
65                  70                  75                  80

Glu Asp Ile Gly Thr Tyr Phe Cys Gln Gln Gly Asn Thr Leu Pro Trp
                85                  90                  95

Thr Gly Phe Phe Phe Thr Lys Leu Glu Ile Lys Arg Gly Gly Gly Gly
            100                 105                 110

Ser Gly Gly Gly Gly Ser Gly Gly Gly Ser Gly Gly Gly Gly Gly Ser
        115                 120                 125

Glu Val Gln Leu Gln Gln Ser Gly Pro Glu Leu Val Lys Pro Gly Ala
    130                 135                 140

Ser Val Lys Ile Ser Cys Lys Ile Asp Ser Gly Tyr Ala Phe Ser Ser
145                 150                 155                 160

Ser Trp Met Asn Trp Val Lys Gln Arg Phe Gly Gln Gly Leu Glu Trp
                165                 170                 175

Ile Gly Arg Ile Tyr Pro Gly Asp Gly Asp Thr Asn Tyr Asn Gly Lys
            180                 185                 190

Phe Lys Gly Lys Ala Thr Leu Thr Ala Asp Lys Ser Ser Thr Ala
        195                 200                 205

Tyr Met Gln Leu Ser Ser Leu Thr Ser Val Asp Ser Ala Val Tyr Phe
    210                 215                 220

Cys Ala Arg Ser Gly Leu Leu Arg Tyr Ala Met Asp Tyr Trp Gly Gln
225                 230                 235                 240

Gly Thr Ser Val Thr Val Ser Ser
                245

<210> SEQ ID NO 2
<211> LENGTH: 248
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 2

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Arg Asn Tyr
            20                  25                  30

```
Leu Asn Trp Tyr Gln Gln Lys Pro Asp Gly Thr Val Lys Leu Leu Ile
            35                  40                  45

Tyr Tyr Thr Ser Arg Leu Gln Pro Gly Val Pro Ser Arg Phe Ser Gly
 50                  55                  60

Ser Gly Ser Gly Thr Asp Tyr Ser Leu Thr Ile Ser Asn Gln Glu Gln
 65                  70                  75                  80

Glu Asp Ile Gly Thr Tyr Phe Cys Gln Gln Gly Asn Thr Leu Pro Trp
                 85                  90                  95

Thr Gly Phe Phe Phe Thr Lys Leu Glu Ile Lys Arg Gly Gly Gly Gly
            100                 105                 110

Ser Gly Gly Gly Gly Ser Gly Gly Gly Ser Gly Gly Gly Gly Ser
            115                 120                 125

Glu Val Gln Leu Gln Gln Ser Gly Pro Glu Leu Val Lys Pro Gly Ala
            130                 135                 140

Ser Val Lys Ile Ser Cys Lys Ile Asp Ser Gly Tyr Ala Phe Ser Ser
145                 150                 155                 160

Ser Trp Met Asn Trp Val Lys Gln Arg Phe Gly Gln Gly Leu Glu Trp
                165                 170                 175

Ile Gly Arg Ile Tyr Pro Gly Asp Gly Asp Thr Asn Tyr Asn Gly Lys
                180                 185                 190

Phe Lys Gly Lys Ala Thr Leu Thr Ala Asp Lys Ser Ser Ser Thr Ala
            195                 200                 205

Tyr Met Gln Leu Ser Ser Leu Thr Ser Val Asp Ser Ala Val Tyr Phe
            210                 215                 220

Cys Ala Arg Ser Gly Leu Leu Arg Tyr Ala Met Asp Tyr Trp Gly Gln
225                 230                 235                 240

Gly Thr Ser Val Thr Val Ser Ser
                245

<210> SEQ ID NO 3
<211> LENGTH: 248
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Arg Asn Tyr
                 20                  25                  30

Leu Asn Trp Tyr Gln Gln Lys Pro Asp Gly Thr Val Lys Leu Leu Ile
            35                  40                  45

Tyr Tyr Thr Ser Arg Leu Leu Pro Gly Val Pro Ser Arg Phe Ser Gly
 50                  55                  60

Ser Gly Ser Gly Thr Asp Tyr Ser Leu Thr Ile Ser Asn Gln Glu Gln
 65                  70                  75                  80

Glu Asp Ile Gly Thr Tyr Phe Cys Gln Gln Gly Asn Thr Leu Pro Trp
                 85                  90                  95

Thr Gly Phe Phe Phe Thr Lys Leu Glu Ile Arg Arg Gly Gly Gly Gly
            100                 105                 110

Ser Gly Gly Gly Gly Ser Gly Gly Gly Ser Gly Gly Gly Gly Ser
            115                 120                 125

Glu Val Gln Leu Gln Gln Ser Gly Pro Glu Leu Val Lys Pro Gly Ala
```

```
            130                 135                 140
Ser Val Lys Ile Ser Cys Lys Ile Asp Ser Gly Tyr Ala Phe Ser Ser
145                 150                 155                 160

Ser Trp Met Asn Trp Val Lys Gln Arg Phe Gly Gln Gly Leu Glu Trp
                165                 170                 175

Ile Gly Arg Ile Tyr Pro Gly Asp Gly Asp Thr Asn Tyr Asn Gly Lys
                180                 185                 190

Phe Lys Gly Lys Ala Thr Leu Thr Ala Asp Lys Ser Ser Thr Ala
                195                 200                 205

Tyr Met Gln Leu Ser Ser Leu Thr Ser Val Asp Ser Ala Val Tyr Phe
        210                 215                 220

Cys Ala Arg Ser Gly Leu Leu Arg Tyr Ala Met Asp Tyr Trp Gly Gln
225                 230                 235                 240

Gly Thr Ser Val Thr Val Ser Ser
                245

<210> SEQ ID NO 4
<211> LENGTH: 248
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 4

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Arg Asn Tyr
                20                  25                  30

Leu Asn Trp Tyr Gln Gln Lys Pro Asp Gly Thr Val Lys Phe Leu Ile
            35                  40                  45

Tyr Tyr Thr Ser Arg Leu Gln Pro Gly Val Pro Ser Arg Phe Ser Gly
        50                  55                  60

Ser Gly Ser Gly Thr Asp Tyr Ser Leu Thr Ile Ser Asn Gln Glu Gln
65                  70                  75                  80

Glu Asp Ile Gly Thr Tyr Phe Cys Gln Gln Gly Asn Thr Leu Pro Trp
                85                  90                  95

Thr Gly Phe Phe Phe Thr Lys Leu Glu Ile Lys Arg Gly Gly Gly Gly
                100                 105                 110

Thr Gly Gly Gly Gly Ser Gly Gly Gly Ser Gly Gly Gly Gly Ser
            115                 120                 125

Glu Val Gln Leu Gln Gln Ser Gly Pro Glu Leu Val Lys Pro Gly Ala
            130                 135                 140

Ser Val Lys Ile Ser Cys Lys Ile Asp Ser Gly Tyr Ala Phe Ser Ser
145                 150                 155                 160

Ser Trp Met Asn Trp Val Lys Gln Arg Phe Gly Gln Gly Leu Glu Trp
                165                 170                 175

Ile Gly Arg Ile Tyr Pro Gly Asp Gly Asp Thr Asn Tyr Asn Gly Lys
                180                 185                 190

Phe Lys Gly Lys Ala Thr Leu Thr Ala Asp Lys Ser Ser Thr Gly
                195                 200                 205

Tyr Met Gln Leu Ser Ser Leu Thr Ser Val Asp Ser Ala Val Tyr Phe
        210                 215                 220

Cys Ala Arg Ser Gly Leu Leu Arg Tyr Ala Met Asp Tyr Trp Gly Gln
225                 230                 235                 240
```

Gly Thr Ser Val Thr Val Ser Ser
                245

<210> SEQ ID NO 5
<211> LENGTH: 248
<212> TYPE: PRT
<213> ORGANISM: Artificial Sequence
<220> FEATURE:
<223> OTHER INFORMATION: Description of Artificial Sequence:  Synthetic
      Peptide

<400> SEQUENCE: 5

Asp Ile Gln Met Thr Gln Thr Thr Ser Ser Leu Ser Ala Ser Leu Gly
  1               5                  10                  15

Asp Arg Val Thr Ile Ser Cys Arg Ala Ser Gln Asp Ile Arg Asn Tyr
             20                  25                  30

Leu Asn Trp Tyr Gln Gln Lys Pro Asp Gly Thr Val Lys Leu Leu Ile
         35                  40                  45

Tyr Tyr Thr Ser Arg Leu Gln Ser Gly Val Pro Ser Arg Phe Ser Gly
 50                  55                  60

Ser Gly Ser Gly Thr Asp Tyr Ser Leu Thr Ile Ser Asn Gln Glu Gln
 65                  70                  75                  80

Glu Asp Ile Gly Thr Tyr Phe Cys Gln Gln Gly Asn Thr Leu Pro Trp
                 85                  90                  95

Thr Gly Phe Phe Phe Thr Lys Leu Glu Ile Lys Arg Gly Gly Gly Gly
            100                 105                 110

Ser Gly Gly Gly Gly Ser Gly Gly Gly Ser Gly Gly Gly Gly Gly Ser
            115                 120                 125

Glu Val Gln Leu Gln Gln Ser Gly Pro Glu Leu Val Lys Pro Gly Ala
            130                 135                 140

Ser Val Lys Ile Ser Cys Lys Ile Asp Ser Gly Tyr Ala Phe Ser Ser
145                 150                 155                 160

Ser Trp Met Asn Trp Val Lys Gln Arg Phe Gly Gln Gly Leu Glu Trp
                165                 170                 175

Ile Gly Arg Ile Tyr Pro Gly Asp Gly Asp Thr Asn Tyr Asn Gly Lys
            180                 185                 190

Phe Lys Gly Lys Ala Thr Leu Thr Ala Asp Lys Ser Ser Ser Thr Ala
            195                 200                 205

Tyr Met Gln Leu Ser Ser Leu Thr Ser Val Asp Ser Ala Val Tyr Phe
        210                 215                 220

Cys Ala Arg Ser Gly Ala Leu Arg Tyr Ala Met Asp Tyr Trp Gly Gln
225                 230                 235                 240

Gly Thr Ser Val Thr Val Ser Ser
                245